United States Patent

Buendia et al.

[11] Patent Number: 5,352,808
[45] Date of Patent: Oct. 4, 1994

[54] PROCESS FOR STEROID PREPARATION

[75] Inventors: Jean Buendia, Le Perreux sur Marne; Michel Vivat, Lagny sur Marne, both of France

[73] Assignee: Roussel Uclaf, France

[21] Appl. No.: 972,228

[22] Filed: Nov. 5, 1992

[30] Foreign Application Priority Data

Nov. 8, 1991 [FR] France .................. 91 13777

[51] Int. Cl.⁵ .............. C07J 7/00; C07J 75/00
[52] U.S. Cl. .................. 552/557; 552/558;
552/559; 552/560; 552/561; 552/562; 552/563;
552/564; 552/565; 552/566; 552/567; 552/568;
552/569; 552/570; 552/571; 552/572; 552/573;
552/574; 552/575; 552/576; 552/577; 552/578;
552/579; 552/580; 552/581; 552/582; 552/583;
552/584; 552/585; 552/586; 552/587; 552/589;
552/590; 552/591; 552/592; 552/593; 552/595;
552/596; 552/597; 552/598; 552/599; 552/600;
552/601; 552/602; 552/603; 552/604; 552/605;
552/606; 552/607; 552/608; 552/609; 552/594.
[58] Field of Search ........... 552/609, 557, 558, 559,
552/560, 561, 562, 563, 564, 565, 566, 567, 568,
569, 570, 571, 572, 573, 574, 575, 576, 577, 578,
579, 580, 581, 582, 583, 584, 585, 586, 587

[56] References Cited

U.S. PATENT DOCUMENTS

| | | | |
|---|---|---|---|
| 4,464,302 | 8/1984 | Nedelec et al. | 260/397.1 |
| 4,565,656 | 1/1986 | Nedelec et al. | 260/397.47 |
| 4,600,538 | 7/1986 | Walker | 260/397.45 |
| 4,720,357 | 1/1988 | Tchernatinsky | 260/397.3 |
| 5,194,602 | 3/1993 | Batisi et al. | 540/29 |
| 5,260,463 | 11/1993 | Brion et al. | 552/577 |

FOREIGN PATENT DOCUMENTS 0175540 9/1985 European Pat. Off. .
0058097 1/1982 France .

*Primary Examiner*—Johann Richter
*Assistant Examiner*—Kimberly J. Kestler
*Attorney, Agent, or Firm*—Bierman and Muserlian

[57] ABSTRACT

A process for the preparation of a compound of the formula

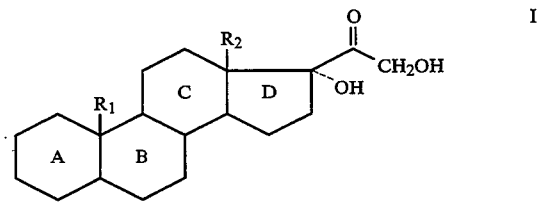

wherein $R_1$ is selected from the group consisting of hydrogen, alkyl of 1 to 4 carbon atoms optionally substituted by halogen or a nitrogen or oxygen function and alkenyl and alkynyl of 2 to 4 carbon atoms, $R_2$ is alkyl of 1 to 4 carbon atoms and the A, B, C and D rings are optionally substituted by at least one member of the group consisting of optionally protected —OH or =O, halogen, alkyl and alkoxy of 1 to 4 carbon atoms and alkenyl and alkynyl of 2 to 4 carbon atoms comprising reacting a compound of the formula

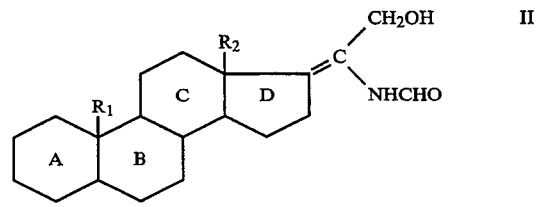

wherein $R_1$ and $R_2$ and the A, B, C and D rings are defined as above with an oxidizing agent in the presence of water and an at least partially water-miscible solvent to obtain a compound of the formula (Abstract continued on next page.)

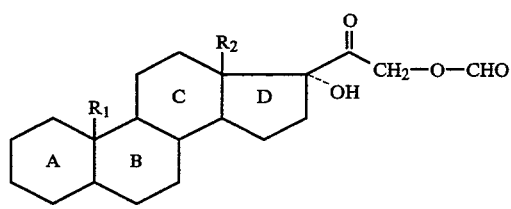
wherein $R_1$ and $R_2$ and the A, B, C and D rings are defined as above, subjecting the latter to a solvolysis in a basic or acidic media and optionally subjecting the product to a deprotection reaction of any protected —OH or =O groups to obtain the compound of formula I and novel intermediates.
15 Claims, No Drawings

PROCESS FOR STEROID PREPARATION

STATE OF THE ART

Relevant prior art includes U.S. Pat. Nos. 4,565,656 and 4,568,492, European application No. 0,336,521, German application No. 2,603,266 and Nedelec et al, J. Chem. Soc., No. 15 (1981), page 775-777.

OBJECTS OF THE INVENTION

It is an object of the invention to provide a novel process for the preparation of compounds of formula I and novel intermediates produced therein.

These and other objects and advantages of the invention will become obvious from the following detailed description.

THE INVENTION

The novel process of the invention for the preparation of a compound of the formula

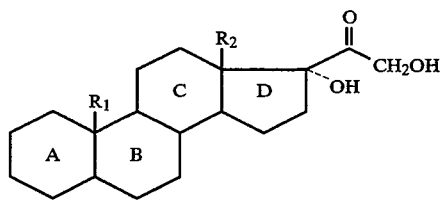

wherein $R_1$ is selected from the group consisting of hydrogen, alkyl of 1 to 4 carbon atoms optionally substituted by halogen or a nitrogen or oxygen function and alkenyl and alkynyl of 2 to 4 carbon atoms, $R_2$ is alkyl of 1 to 4 carbon atoms and the A, B, C and D rings are optionally substituted by at least one member of the group consisting of optionally protected —OH or =O, halogen, alkyl and alkoxy of 1 to 4 carbon atoms and alkenyl and alkynyl of 2 to 4 carbon atoms comprises reacting a compound of the formula

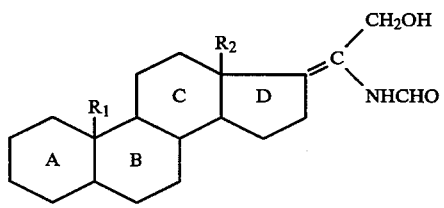

wherein $R_1$ and $R_2$ and the A, B, C and D rings are defined as above with an oxidizing agent in the presence of water and an at least partially water-miscible solvent to obtain a compound of the formula

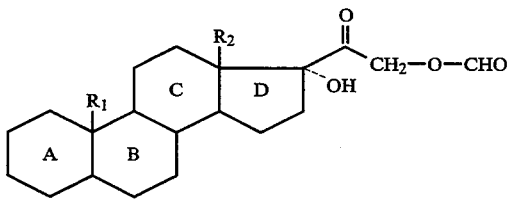

wherein $R_1$ and $R_2$ and the A, B, C and D rings are defined as above, subjecting the latter to a solvolysis in a basic or acidic media and optionally subjecting the product to a deprotection reaction of any protected —OH or =O groups to obtain the compound of formula I.

When $R_1$ is alkyl, it is preferably methyl or ethyl and when $R_1$ is alkyl substituted by an oxygen or nitrogen group, it is preferably hydroxymethyl, hydroxyethyl, formyl, acetyl, —CN, aminomethyl or aminoethyl. When $R_1$ is alkyl substituted by halogen, it is preferably —CH$_2$Hal where Hal is chlorine, bromine or fluorine. When $R_1$ is alkenyl or alkynyl, it is preferably vinyl, allyl or ethynyl. $R_2$ is preferably methyl or ethyl.

When the A, B, C and D rings have double bonds, they are preferably in the 1(2), 3(4), 4(5) or 9(11) position or are conjugated double bonds in the 3(4) and 5(6) positions or in the 4 (5) and 6(7) positions or in the 1(2) and 4(5) positions or an aromatic system of 3 double bonds in the 1, 3 and 5 positions or 1(2), 4(5) and 6(7) positions.

When the A, B, C and D rings are substituted by at least one hydroxyl, it is preferably hydroxyl in position 3, 9 or 11. When the hydroxyl function is protected, it is preferably a protection in the form of organic acid esters such as acetic acid or formic acid, or lower alkyl ethers such as methyl or ethyl ether, silylated ethers such as trialkylsilyl like trimethyl- or dimethyl-tert-butylsilyl, triarylsilyl such as triphenylsilyl or diarylalkylsilyl such as diphenyl-tert-butylsilyl, or tetrahydropyranyl ether.

When the A, B, C and D rings are substituted by at least one ketone function, it is preferably a ketone in position 3 or 11. When the ketone function in position 3 is protected, it is preferably a protection in the form of a cyclic or non-cyclic ketal or thioketal or of an enol ether or also of an oxime. When the ketone function in position 11 is protected, it is preferably a protection in the form of an enol ether.

When the A, B, C and D rings are substituted by at least one halogen, it is preferably fluorine, chlorine or bromine in position 6 or 9α. When the A, B, C and D rings are substituted by at least one alkyl, it is preferably methyl or ethyl in position 2, 6, 7, 16α or 16β-position. When the A, B, C and D rings are substituted by at least one alkoxy, it is preferably methoxy or ethoxy in position 3 or 11β.

When the A, B, C and D rings are substituted by at least one alkenyl, it is preferably vinyl or allyl in position 11β, for example and when the A, B, C and D rings are substituted by at least one alkynyl, it is preferably ethynyl in position 11 β for example.

In a preferred mode of the process of the invention, the compound of formula II has the formula

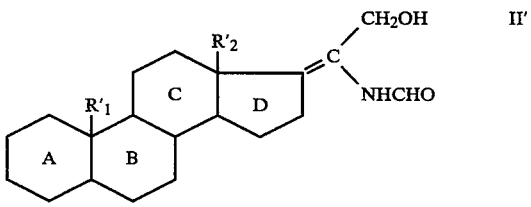

wherein $R'_1$ is hydrogen or methyl, $R'_2$ is methyl or ethyl, the A, B, C and D rings optionally carry at least one double bond in position 1(2), 3(4), 4(5) or 9(11) or 3(4) and 5(6) or 4(5) and 6(7) or 1(2) and 4(5) or 1, 3, 5 or 1(2), 4(5) and 6(7) and are optionally substituted by at least one hydroxyl in position 3, 9 and/or 11, by at least one ketone in position 3 and/or 11, by at least one fluorine, chlorine or bromine in position 6 and/or 9, by at least one methyl or ethyl in position 2, 6, 7 and/or 16 α or 16 β, by at least one methoxy or ethoxy in position 3 and/or 11β, by vinyl or allyl in position 11β or by ethynyl in position 11β.

A more preferred process of the invention uses a compound of formula II having the formula

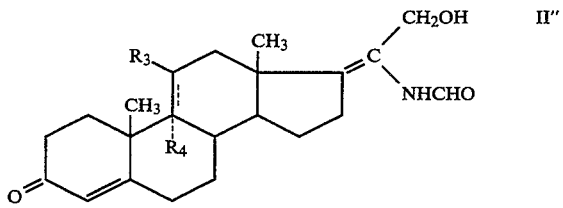

in which either the dotted line in position 9(11) is a second bond and R₃ and R₄ are hydrogen, or the dotted line is not a second bond and R₃ is hydrogen, β—OH or oxo and R₄ is hydrogen or R₃ is hydrogen and R₄ is α—OH.

Preferably, the starting compound of formula I has a formula selected from the group consisting of

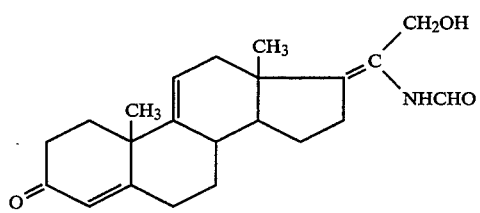

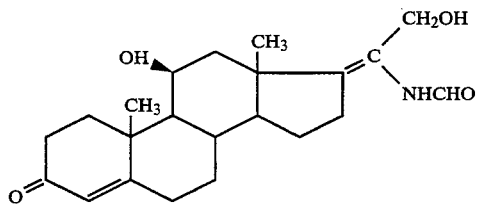

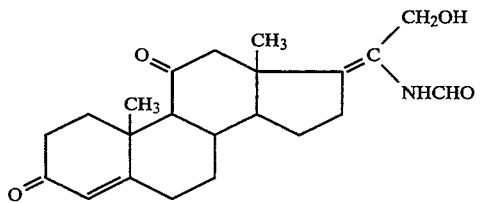

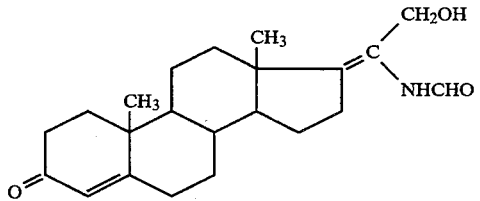

and

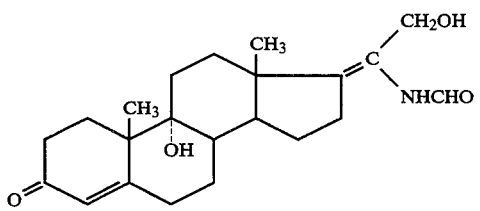

The oxidizing agent can be selected from the group consisting of peracids such as perbenzoic acid, meta-chloroperbenzoic acid, peracetic cid, persuccinic acid, perphthalic acid, performic acid or pertungstic acid, hydrogen peroxide alone or in the presence of hexachloro- or hexafluoroacetone or hydroperoxides such as tertbutyl hydroperoxide in the presence of vanadium acetylacetonate in catalytic quantity. The peracids, and especially perphthalic acid are preferred. The peracid may be prepared extemporaneously by the action of hydrogen peroxide on the corresponding acid or anhydride.

The solvent may be an alcohol such as methanol, ethanol, isopropanol, an ether such as tetrahydrofuran, dioxane, an ester such as ethyl acetate, a ketone such as acetone, methyl ethyl ketone, an amide such as dimethylformamide as well as acetonitrile or acetic acid. The alkanols are preferred.

The reaction can optionally be carried out in the presence of a phase transfer agent such as triethylbenzyl-ammonium chloride or tetrabutyl-ammonium bromide. The solvolysis of the compound of formula III is preferably an alcoholysis carried out in the presence of a base such as an alkali metal hydroxide like sodium hydroxide or potassium hydroxide or an alkali metal carbonate such as sodium or potassium carbonate, or in the presence of a strong aqueous acid such as hydrochloric acid, hydrobromic acid, sulfuric acid or acetic acid. The base can be used in catalytic quantity. The alcohol used is preferably methanol or ethanol. The solvolysis can also be a hydrolysis carried out by using the above bases.

As is indicated above, there can be used at the start of the process of the invention a compound of formula II in which the optionally present hydroxyl and ketone functions are protected. It goes without saying that according to the nature of the protective group or groups, that is whether or not they are sensitive in a basic or acidic medium, the compounds of formula III then I obtained will be able to contain the deprotected functions and that if it is desired to avoid this, a suitable protection can be chosen.

Preferably the reaction is carried out without intermediate isolation of the compound of formula III. The preferred implementation conditions are the same as those that were specified above. It may be preferable to neutralize the oxidizing agent of the medium before the solvolysis of the formate of formula III.

The compounds of formula II are generally known and are described in European Patent No. 0,023,856. Some of the compounds containing hydroxy or ketone functions may only have been described in a protected form or in the deprotected form. It is of course within the capability of a man skilled in the art to prepare one form or another from the known compound.

The oxidation of the ene-amides of formula II by peracids has already been the subject of tests in the past, for the purpose of preparing compounds of formula I. Nedelec et al J. Chem. Soc., Chem. Comm. (1981) page 775 is an example wherein tests on a compound containing an aromatic ring were unsuccessful because they led to the cutting of the chain in position 17 giving a corresponding 17-oxo derivative. Another test of this type applied to a $\Delta^{4,17(20)}$-pregnadien-3-one has been described in the experimental part.

According to the above publication, the introduction of an oxygenated function in position 17 had only been possible by using a specific reagent, lead tetracetate, by a method described by Barton et al J. Chem. Soc. Perkin., Trans. 1, (1975), page 1242. This method led intermediately to a diacetate in position 17 α, 21 and was also used to oxidize a 9 α—OH derivative in European Patent Application No. 0,336,521 and the reagent is preferably used in an anhydrous medium.

It turns out in fact that the specific enamide chain formation in position 17 is extremely fragile vis-a-vis oxidants and particularly peracids. It has been acknowledged since the publication of Nedelec et al that those enamides which constitute the best intermediates in the reconstitution of the chain in position 17 of the cortisones necessitated the use of a specific reagent, which is an hydroxylation reagent and not an oxidation reagent.

The process of the present Application has demonstrated that it is possible under conditions which are not obvious in this type of reaction, namely in the presence of water, to oxidize with good yields the enamides of formula II, particularly with peracids, therefore under industrial conditions to obtain the corresponding 17α, 21-diol derivatives. The process lead intermediately to a monoformate in position 21 [compound III] that is very easy to hydrolyze, particularly by an alcoholysis in a basic or acidic medium.

The novel intermediates of the invention have the formula

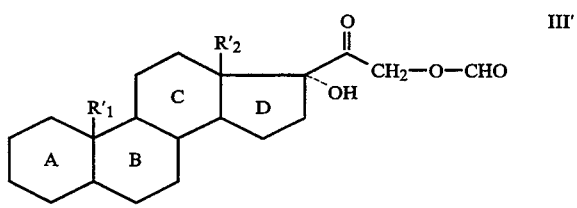

III' wherein R'$_1$, R'$_2$ and the A, B, C and D rings are defined as above with the exception of the compound wherein R'$_2$ is methyl and either R'$_1$ is methyl two double bonds are present in position 1 and 4, an oxo in position 3, hydroxy or oxo in position 11 or hydroxy in position 11 and methyl in position 16 β, or R'$_1$ is methyl, a double bond is present in position 4, keto is in position 3 and hydrogen, a hydroxy or oxo is in position 11, or R'$_1$ is methyl, hydroxy is present in position 3 and an oxo is in position 11, or R'$_1$ is hydrogen, a double bond is present in position 4 and a keto function in position 3.

The preferred compounds of formula III' have the formula

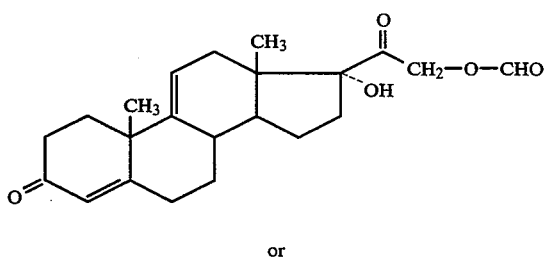

or

-continued

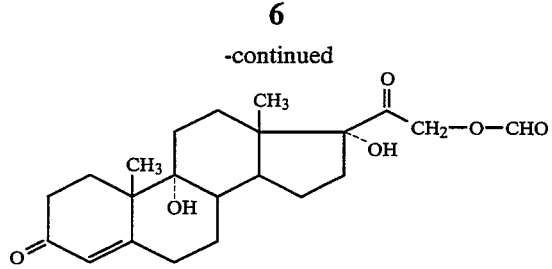

The compounds of formula I are known therapeutics or are known intermediates for the preparation of therapeutics.

In the following examples, there are described several preferred embodiments to illustrate the invention. However, it is to be understood that the invention is not intended to be limited to the specific embodiments.

EXAMPLE 1

Δ$^4$-pregnene-11β, 17α, 21-triol-3,20-dione (Hydrocortisone)

STEP A: 21-formyloxy-Δ$^4$-pregnene-11β, 17α-diol-3,20-dione 0.81 g of 20-formamido-Δ$^{4,17(20)}$-pregnadien-11β, 21-diol-3-one, 6.4 ml of water and 6.4 ml of methanol were mixed together under an inert gas atmosphere and 0.8 ml of 50% perphthalic acid (obtained from 2 g of phthalic anhydride solubilized at 40° C. over 15 minutes in a mixture of 1 ml of 50% hydrogen peroxide and 2 ml of methanol) were added with stirring at 22°-23° C. Then after 90 minutes of stirring, another 0.8 ml of perphthalic acid was added. After 4 hours, another 0.5 ml of perphthalic acid was added and after 3 hours of stirring, the mixture was cooled to 5° C. The crystals were separated and washed with water and with an aqueous solution of sodium bicarbonate and dried to obtain 0.586 g of the expected product.

IR Spectrum (nujol):

Absorption at 3420 and 3315 cm$^{-1}$ (OH), 1735, 1715 and 1625 cm$^{-1}$ (C=O formate, 20-keto and delta 4-3-keto) .

NMR Spectrum (DMSO):

18-CH$_3$:0.77 (s); 19-CH$_3$:1.37 (s); H$_{11}$:4.27 (m); 1H (mobile): 4.36 (d) and 5.44 (s); CO—CH$_2$—O:4.83 (d) and 5.18 (d); H$_4$:5.56 (s); —CHO: 8.33 (s).

STEP B: Δ$^4$-pregnene-11β, 17α, 21-triol-3,20-dione (Hydrocortisone)

0.575 g of the product of Step A and 10 ml of methanol were mixed together under an inert gas atmosphere and then 0.05 g of potassium carbonate was added. The mixture was stirred for 30 minutes and then 0.7 ml of 1N sulfuric acid was added. Concentration was carried out under reduced pressure and the residue was chromatographed on silica. Elution with a chloroform - methanol mixture (95–5) yielded 0.502 g of hydrocortisone melting at 210° C. and with a specific rotation of [α]$_D$ =+151.6° (c=1% in EtOH).

EXAMPLE 2

Test in anhydrous medium 0.05 g of 20-formamido-Δ$^{4,17(20)}$-pregnadien-11β, 21-diol-3-one and 0.5 ml of methanol were mixed together under an inert gas atmosphere and 0.05 g of perphthalic acid was added at ambient temperature. The mixture was stirred for 20 hours and the chromatographic analysis of the reaction medium in the solvent system methylene chloride - methanol (95–5) revealed the absence of the starting product, and the total absence of hydrocortisone-21-formate. The presence of $\Delta^4$-androsten-11$\beta$-ol-3,17-dione in a large quantity was identified by comparison with a reference sample with a Rf=0.39.

NMR Spectrum (CDCl$_3$, 300 MHz):
1.17 (s): 18-CH$_3$; 1.47 (s): 19-CH$_3$; 4.47 (q): H$_{11}$ equatorial; 5.70 (d):H$_4$.

Preparation: 20-formamido-$\Delta^{4,17(20)}$-pregnadien,11$\beta$, 21-diol-3-one 9 g of 3-ethoxy-20-formamido-$\Delta^{3,5,17(20)}$-pregnatriene-11$\beta$, 21-diol (described in European Patent No. 023,856) were dissolved in 90 ml of acetic acid with 5% water and the mixture was stirred for 30 minutes at ambient temperature under an inert gas atmosphere. The mixture was cooled to about 0° C. and 140 ml of 22° Be ammonium hydroxide were added slowly. Extraction was carried out with chloroform and the organic phase was washed with water, dried and brought to dryness to obtain 8.1 g of the expected product which was purified by chromatography on silica and eluting with a chloroform - methanol mixture (95–5) to obtain the product melting at approx 238° C. and with a specific rotation of $[\alpha]_D = +91° \pm 2.5°$ (c=0.5% in ethanol).

IR Spectrum (nujol):
Absorptions at 3435–3242 cm$^{-1}$ (NH/OH); 1665–1655 cm$^{-1}$ (C=O); 1610–1523 cm$^{-1}$ (C=C conjugated-NH deformation).

EXAMPLE 3

$\Delta^4$-pregnene-17$\alpha$, 21-diol-3,20-dione

STAGE A: 21-formyloxy-$\Delta^4$-pregnene-17$\alpha$,-ol-3,20-dione 2 g of 20-formamido$\Delta^{4,17(20)}$-pregnadiene-21-ol-3-one in 20 ml of water and 20 ml of methanol were stirred at ambient temperature and 7 ml of peracid obtained from 2.66 g of perphthalic anhydride, 4 ml of methanol and 1.9 ml of 50% hydrogen peroxide were introduced slowly over three and a half hours at 23° C. The mixture was stirred for 2 hours and the reaction medium was stirred while 20 ml of water were added over one hour. The suspension was stirred followed by separating, washing with a methanol - water (1–1) mixture and drying under reduced pressure to obtain 1.4 g of crude product which was chromatographed on silica (eluant: methylene chloride - methanol 85–15 then 80–20) to obtain 0.9 g of the expected product melting at 186° C.
IR Spectrum
Absorptions at 3615 cm$^{-1}$ OH (+associated);

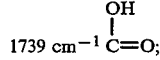

1722 cm$^{-1}$ 20-keto; 1661 cm$^{-1}$ 13-keto $\Delta^4$; 1615 cm$^{-1}$ C=C.

STEP B: $\Delta^4$-pregnene-17$\alpha$, 21-diol-3,20-dione 0.27 g of the product of Step A in 5 ml of methanol were mixed for 30 minutes under an inert atmosphere and then 20 mg of potassium carbonate were added. The mixture was stirred for 30 30 minutes and 10 ml of water were added. The mixture was stirred for 10 minutes and the precipitate was separated, washed with water and dried under reduced pressure to obtain 0.204 g of the expected product.

IR Spectrum (CHCl$_3$):
Absorption at 3615 cm$^{-1}$ (OH); 1708–1661 cm$^{-1}$ (C=O); 1615 cm$^{-1}$ (C=C).

Preparation of 20-formamido-$\Delta^{4,17(20)}$-pregnadien-21-ol-3-one

STEP A: 3-ethoxy- $\Delta^{3,5}$-androstadien-17-one 50 g of $\Delta^4$-androstene-3,17-dione in 150 ml of ethanol were stirred at 65° C. under an inert atmosphere in the presence of 50 ml of ethyl orthoformate and after complete solubilization, 2.5 ml of an ethanolic solution of sulfuric acid (0.2 ml/100 ml) were added. After reacting for one hour while allowing the temperature to return to 60° C. then to 50° C. crystallization was started followed by cooling to 25° C. over 90 minutes. 10 ml of water were added and the mixture was stirred for one and a half hours. Another 10 ml of water were added and the mixture was stirred for 40 minutes. The precipitate was separated out, washed with a water - alcohol 25–75, then 50–50 mixture and dried under reduced pressure to obtain 46.5 g of the expected product.

IR Spectrum (CHCl$_3$):
Absorption at 1732 cm$^{-1}$ (17 keto);

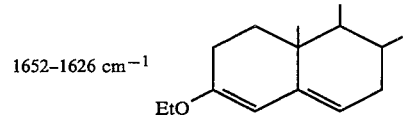

1652–1626 cm$^{-1}$

STEP B: Ethyl 3-ethoxy-20-formamido- ;$\Delta^{3,5,17(20)}$-pregnatrien-21-oate 7 g of potassium tert-butylate were dissolved in 38 ml of tetrahydrofuran and the mixture was cooled to 0°/+5° C. 6.8 ml of ethyl isocyanoacetate in solution in 38 ml of tetrahydrofuran were added over 20 minutes and the mixture was stirred for 15 minutes. 15 g of the product of Step A in 75 ml of tetrahydrofuran were added over 30 minutes and the mixture was held at 0°/+5° C. for 4 hours. An aqueous solution of ammonium chloride (7.5 g/75 ml) was added, followed by partial concentration under reduced pressure at ambient temperature. 80 ml of water were added to the suspension formed and the precipitate was separated, washed with water and dried under reduced pressure at 35° C. to obtain 20.7 g of the expected product.

IR Spectrum (CHCl$_3$):
Absorptions at 3415 and 3390 cm$^{-1}$ (NH); 1695 cm$^{-1}$ (C=O); 1652 and 1625 cm$^{-1}$ (C=C).

STEP C: 20-formamido- $\Delta^{4,17(20)}$-pregnadien-21-ol-3-one 10 ml of lithium aluminium hydride in 100 ml of tetrahydrofuran were cooled to $-5°$ C. under an inert atmosphere and 10 g of the product of Step B were added. The mixture was stirred for one and a half hours at 0° C. and 2 g of ammonium chloride were added. Then, 40 ml of a 25% solution of ammonium chloride were added over 50 minutes while allowing the temperature to return to about 10° C. The mixture was stirred for 15 minutes and then the precipitate was separated. The solid was washed with a methylene chloride methanol (1–1) mixture and the solvent was evaporated. 10 g of the crude product were taken up in 50 ml of chloroform and 5 ml of water and 5 ml of acetic acid were added. The mixture was stirred for 1 hour and another 5 ml of acetic acid were added. The mixture was stirred for 5 hours and was then neutralized by the addition of 2N sodium hydroxide followed by decanting. The aqueous phase was extracted with methylene chloride and the extracts were dried and the solvent was eliminated under reduced pressure. After chromatography on silica (eluant: methylene chloride - isopropanol 3% to 12%), 2.75 g of the expected product were obtained.

IR Spectrum ( $CHCl_3$ ):
Absorption at 3610 cm$^{-1}$ (OH); 3440 cm$^{-1}$ (NH); 1672 cm$^{-1}$ (conjugated ketone +formyl); 1616 cm$^{-1}$ (C=C)

EXAMPLE 4

$\Delta^{4,9(11)}$-pregnadiene-17α, 21-diol-3,20-dione

STEP A: 21-formyloxy-$\Delta^{4,9,(11)}$-pregnadiene-17α-ol-3,20-dione 0.4 g of 20-formamido-$\Delta^{4,9(11), 17(20)}$-pregnatrien-21-ol-3-one in 4 ml of water and 2 ml of methanol were stirred at ambient temperature and 1.2 ml of peracid obtained from 0.532 g of perphthalic anhydride, 0.8 ml of methanol and 0.4 ml of 50% hydrogen peroxide were introduced slowly over four and a half hours at 23° C. The mixture was stirred at 45° C. and then 4 ml of water were added over one hour with stirring. The suspension was stirred for 30 minutes, separated, washed with a methanol - water (75-25) mixture and dried under reduced pressure to obtain 0.18 g of crude product containing a mixture of the expected product and the corresponding α- $\Delta^{9(11)}$-epoxide.

IR Spectrum:
Absorptions at 3614 cm$^{-1}$ OH (+associated); 1740 cm$^{-1}$: formyl; 1722 cm$^{-1}$ 20-keto; 1666 cm$^{-1}$ 3-keto $\Delta^4$; 1616 cm$^{-1}$: C=C.

STEP B: $\Delta^{4,9,(11)}$-pregnadiene-17α, 21-diol-3,20-dione 100 mg of the mixture of Step A were mixed with 1.9 ml of methanol for 30 minutes under an inert atmosphere and 7.2 mg of potassium carbonate were added. The mixture was stirred for 30 minutes and then 5 ml of water were added. The mixture was stirred for 15 minutes and the precipitate was separated, washed with water and dried under reduced pressure to obtain after chromatography on silica (eluant: chloroform - isopropanol 95-5), 43 mg of the expected product and 35 mg of the corresponding α- $\Delta^{9(10)}$ epoxide.

IR Spectrum ($CHCl_3$) of cortinene:
Absorption at 3520-3480 cm$^{-1}$ (OH); 1710-1660 cm$^{-1}$ (C=O); 1610 cm$^{-1}$ (C=C).

Preparation of 20-formamido-$\Delta^{4,9(11), 17(20)}$-pregnatrien-21-ol-3-one

STEP A: 3-ethoxy-$\Delta^{3,5,9(11)}$-androstatrien-17-one

Using the procedure of Step A of Preparation 3, 50 g of $\Delta^{4,9(11)}$-androstadiene-3,17-dione were reacted to obtain 37.4 g of the expected product.

IR Spectrum ($CHCl_3$):
Absorption at 1732 cm$^{-1}$(17-keto); 1656-1629 cm$^{-1}$ (3(EtO) 3,5-diene).

STEP B: Ethyl 3-ethoxy-20-formamido-$\Delta^{3,5,9(11), 17(20)}$-pregnatetraene-21-oate Using the procedure of Step B of Preparation 3, 15 g of the product of Step A were reacted to obtain 20.1 g of the expected product.

IR Spectrum ($CHCl_3$):
Absorptions at 3417 and 3389 cm$^{-1}$ (NH); 1697 cm$^{-1}$ (C=O); 1656 and 1629 cm$^{-1}$ (C=C).

STEP C: 3-ethoxy-20-formamido-$\Delta^{3,5,9(11), 17(20)}$-pregnatetraene 2.5 g of the enamide of Step B were added over 30 minutes to 2.8 ml of lithium aluminium hydride in 25 ml of tetrahydrofuran cooled to 0°/−5° C. and the mixture was stirred for 15 minutes. 1.6 ml of monosodium phosphate in aqueous solution (30%) were added over 45 minutes and 10 ml of tetrahydrofuran were added. The suspension was stirred for one and a half hours while allowing the temperature to return to ambient temperature. After filtering and washing with a tetrahydrofuran - chloroform 1-1 mixture, then with a chloroform - ethanol 2-1 mixture, the solvents were evaporated from the filtrate. The residue was chromatographed on silica (eluant: methylene chloride - isopropanol 92.5-7.5 with 2°/°$_{oo}$ triethylamine) to obtain 1.49 g of the expected product.

IR Spectrum ($CHCl_3$):
Absorptions at 3437 cm$^{-1}$ (NH); 1608 cm$^{-1}$ (C=O); 3612 cm$^{-1}$ (OH); 1657 and 1629 cm$^{-1}$3 (EtO) 3,5-diene.

STEP D: 20-formamido-$\Delta^{4,9(11), 17(20)}$-pregnatrien-21-ol-3-one 1 g of the product of Step C in 5 ml of water with 5 ml of 99.5% acetic acid added to it were stirred for 3 and a half hours under an inert atmosphere. The mixture was poured into a water/ice mixture and 2.9 g of sodium bicarbonate were added. The aqueous phase was extracted with methylene chloride and the extracts were dried. The solvent was evaporated and the residue was chromatographed on silica (eluant: methylene chloride - isopropanol 92-8) to obtain 0.55 g of the expected product.

Various modifications of the process of the invention may be made without departing from the spirit or scope thereof and it is to be understood that the invention is intended to be limited only as defined in the appended claims.

What we claim is:

1. A process for the preparation of a compound of the formula

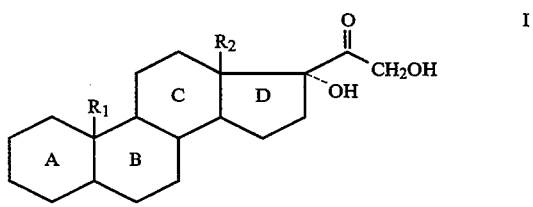

wherein $R_1$ is selected from the group consisting of hydrogen, alkyl of 1 to 4 carbon atoms optionally substituted by halogen or a nitrogen or oxygen function and alkenyl and alkynyl of 2 to 4 carbon atoms, $R_2$ is alkyl of 1 to 4 carbon atoms and the A, B, C and D rings are optionally substituted by at least one member of the group consisting of optionally protected —OH or =O, halogen, alkyl and alkoxy of 1 to 4 carbon atoms and alkenyl and alkynyl of 2 to 4 carbon atoms comprising reacting a compound of the formula

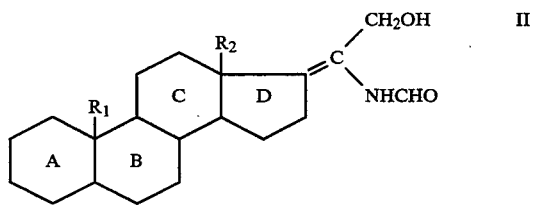

wherein R₁ and R₂ and the A, B, C and D rings are defined as above with an oxidizing agent in the presence of water and an at least partially water-miscible solvent to obtain a compound of the formula

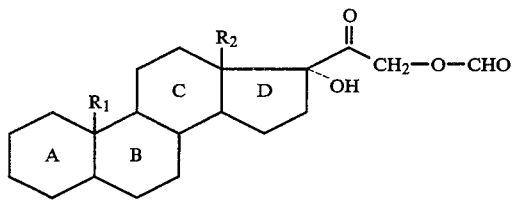

wherein R₁ and R₂ and the A, B, C and D rings are defined as above, subjecting the latter to a solvolysis in a basic or acidic media and optionally subjecting the product to a deprotection reaction of any protected —OH or =O groups to obtain the compound of formula I.

2. The process of claim 1 wherein the compound of formula II has the formula

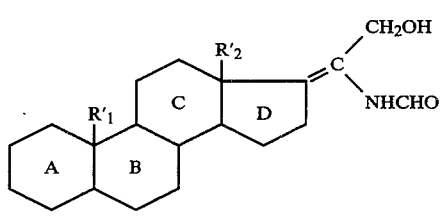

wherein R'₁ is hydrogen or methyl, R'₂ is methyl or ethyl and the A, B, C and D rings optionally have double bonds in the 1(2), 3(4), 4(5) or 9(11) positions; or 3(4) and 5(6); or 4(5) and 6(7); or 1(2) and 4(5) positions; or 1, 3, 5 or 1(2), 4(5) and 6(7) positions and optionally substituted by hydroxy in at least one of the 3, 9 and 11 positions, by ketone in at least one of the 3 and 11 positions, by fluorine, bromine or chlorine in at least one of the 6 and 9 positions, by methyl or ethyl in at least one of the 2, 6, 7 and 16α or 16β positions, by methoxy or ethoxy in at least one of 3 and 11 positions and by vinyl or allyl or ethynyl in the 16β position.

3. The process of claim 1 wherein the compound of formula II has the formula

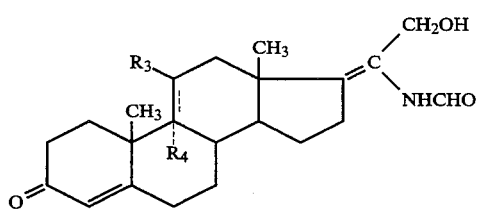

wherein either the dotted line in position 9(11) is a second bond and R₃ is hydrogen or the dotted line is not a second bond and R₃ is hydrogen, β-hydroxy or oxo and R₄ is hydrogen, or R₃ is hydrogen and R₄ is α—OH.

4. The process of claim 1 wherein the compound of formula II is

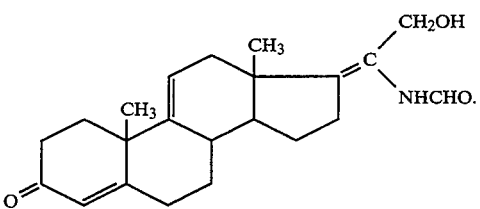

5. The process of claim 1 wherein the compound of formula II is

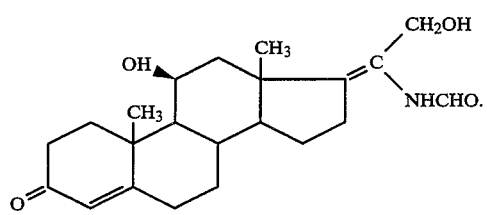

6. The process of claim 1 wherein the compound of formula II is

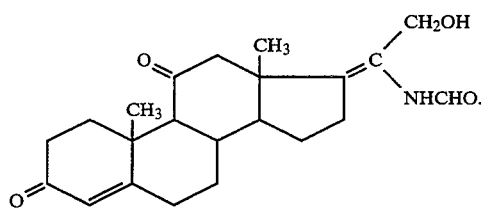

7. The process of claim 1 wherein the compound of formula II is

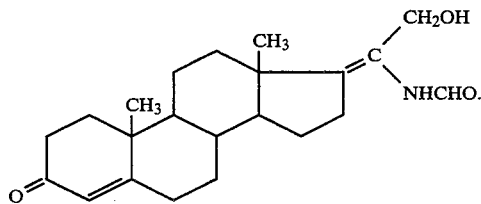

8. The process of claim 1 wherein the compound of formula II is

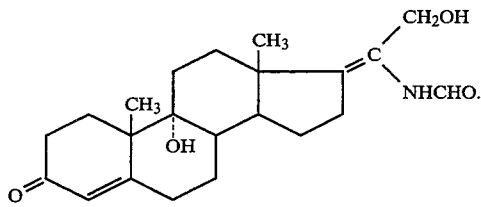

9. The process of claim 1 wherein the oxidation agent is selected from the group consisting of peracids, hydrogen peroxide and hydroperoxides.

10. The process of claim 9 wherein the oxidation agent is a peracid.

11. The process of claim 9 wherein the oxidation agent is perphthalic acid.

12. The process of claim 1 wherein the reaction is carried out in an alkanol.

13. The process of claim 1 wherein the solvolysis of the compound of formula III is an alcoholysis carried out in the presence of an alkali metal hydroxide or carbonate.

14. The process of claim 1 wherein the solvolysis of the compound of formula III is an alcoholysis carried out in the presence of a strong aqueous acid.

15. The process of claim 1 wherein the reaction is carried out without intermediate isolation of the compound of formula III.

* * * * *